United States Patent [19]

Kiel

[11] Patent Number: 4,870,002

[45] Date of Patent: Sep. 26, 1989

[54] METHOD OF PREVENTION OF OXIDATIVE INJURY TO CELLS

[75] Inventor: Johnathan L. Kiel, San Antonio, Tex.

[73] Assignee: The United States of America as represented by the Secretary of the Air Force, Washington, D.C.

[21] Appl. No.: 804,819

[22] Filed: Dec. 4, 1985

Related U.S. Application Data

[60] Continuation-in-part of Ser. No. 652,370, Sep. 19, 1984, Pat. No. 4,766,150, which is a division of Ser. No. 251,694, Apr. 7, 1981, Pat. No. 4,486,408.

[51] Int. Cl.$^4$ .......................... A01N 1/02; C12N 5/00
[52] U.S. Cl. ........................................ 435/2; 424/101; 435/240.2; 435/240.25
[58] Field of Search ...................... 514/561; 435/240.2, 435/2, 240.25; 424/101

[56] References Cited

PUBLICATIONS

Chemical Abstracts Chemical Substance Index 11th Collective vol.–96–105 (1982–1986) p. 58964 CS.
Huang et al, Chem. Abst. vol. 67 (1967), p. 9082u.
Hagino et al, Chem. Abst. vol. 79 (1973) p. 135256q.
Rout–Chem. Abst. –vol. 63 (1965), p. 2164f.
Huang–J. Pharmacol. Exptl. Therap. vol. 134, (1961) pp. 257–265.
Lefkowitz, Doris L. et al, "Activation of Macrophages with Oxidative Enzymes," Methods in Enzymology, vol. 132, 1986, pp. 537–548.
Kiel, Johnathan L. et al, "Physiologic Aging of Mature Porcine Erythrocyutes: Effects of Various Metabolites, Antimetabolites, and Physical Stressors," Am. J. Vet. Res., vol. 47, No. 10, Oct. 1986, pp. 2155–2160.
Kiel, Johnathan L. et al, "3–Amino-L-tyrosine and Its Derivatives as Anti-Inflammatory and Immunosuppressive Compounds," Medicine & Biology, 1987, p. 190.
Pruett, S. B. et al, "Relationship Between Oxidative Metabolism and Thiol Production in Macrophage-Like Cell Lines", Federation of American Societies for Experimental Biology, 72nd Annual Meeting, Las Vegas, Nevada, May 1–5, 1988, p. 3611.

*Primary Examiner*—Sam Rosen
*Attorney, Agent, or Firm*—Stanton Collier; Donald J. Singer

[57] ABSTRACT

A process for preventing oxidative injury in which living cells are contacted with a protective amount of 3-amino-tyrosine or a derivative thereof. Also provided is a process for preserving a cell sample involving collecting a sample of cells and adding 3-aminotyrosine or a derivative thereof to that cell sample. A process for preventing thermal damage to living cells is also provided which comprises contacting the cells with a thermal protectant amount of 3-aminotyrosine or a derivative thereof, as is a process for protecting living cells from damage caused by ionizing radiation, which comprises contacting the cells with a radioprotectant amount of 3-aminotyrosine or a derivative thereof. Also provided is a process for suppressing anti-inflammatory reactions in animals which comprises administering an anti-inflammatory amount of 3-aminotrosine or a derivative thereof to an animal.

6 Claims, 4 Drawing Sheets

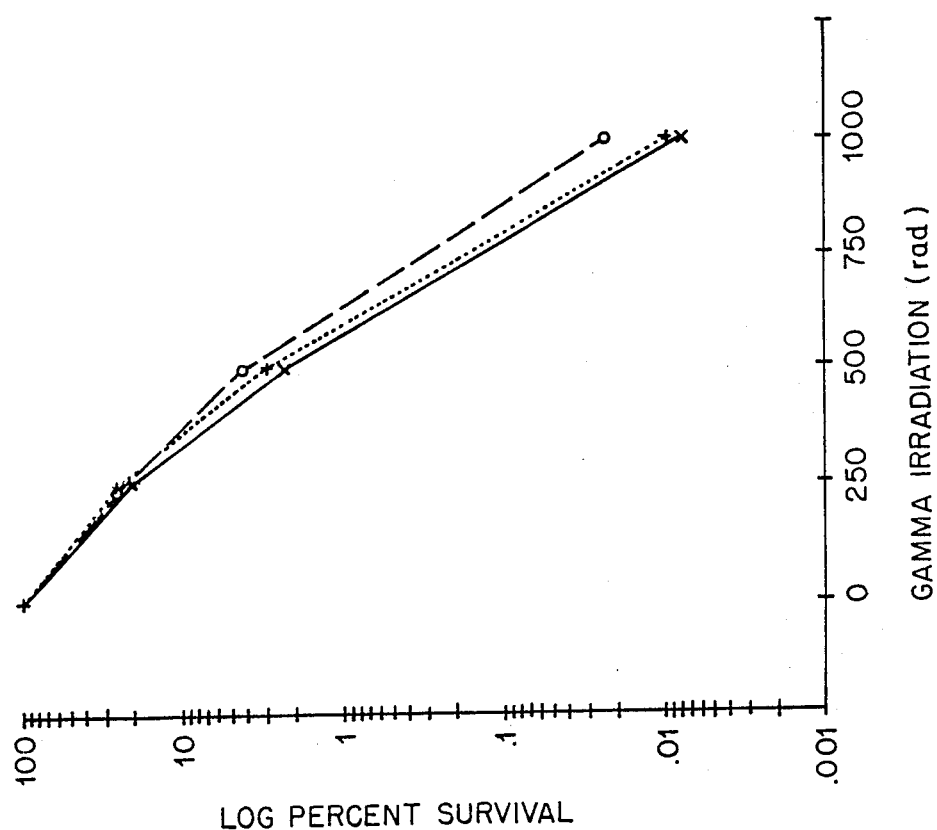
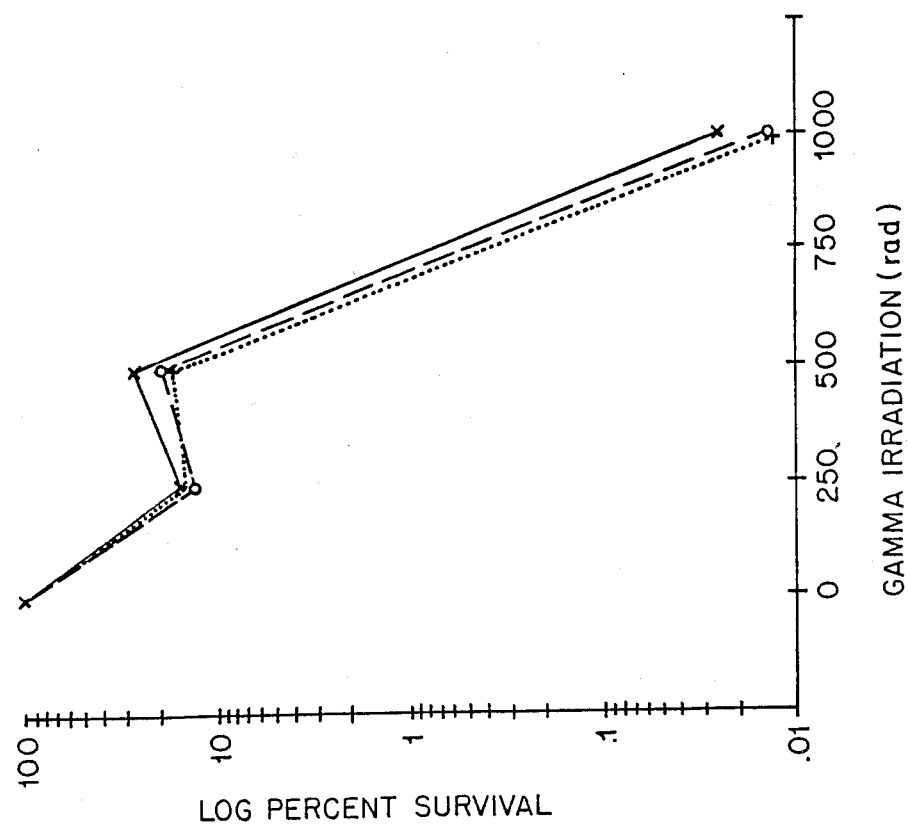

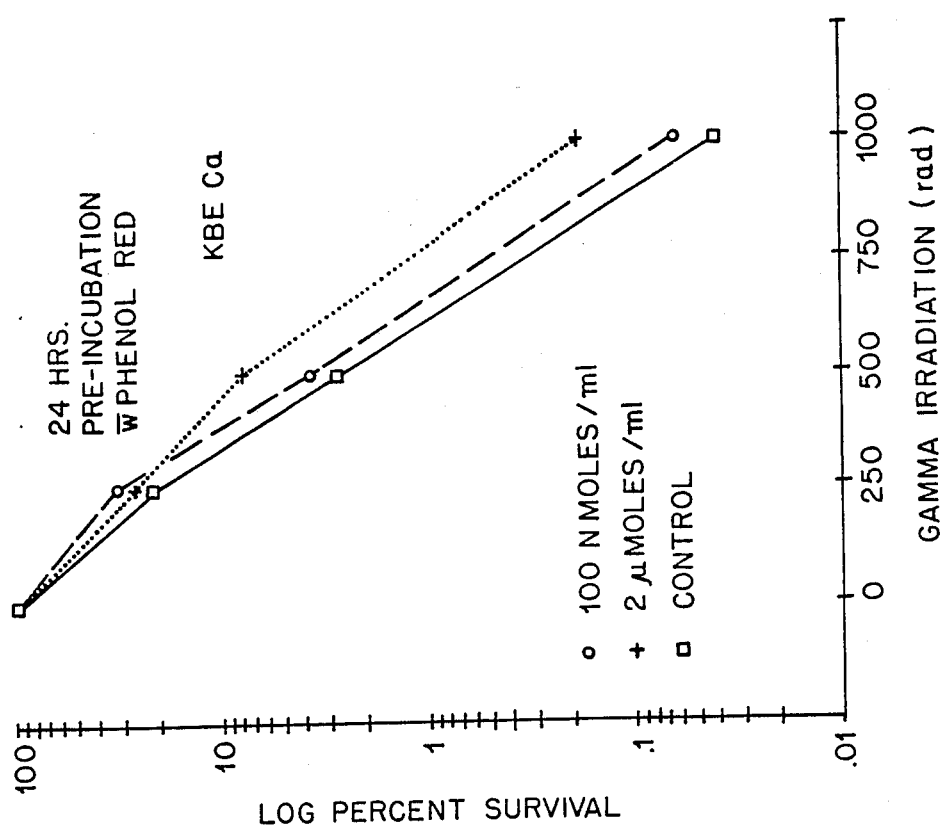
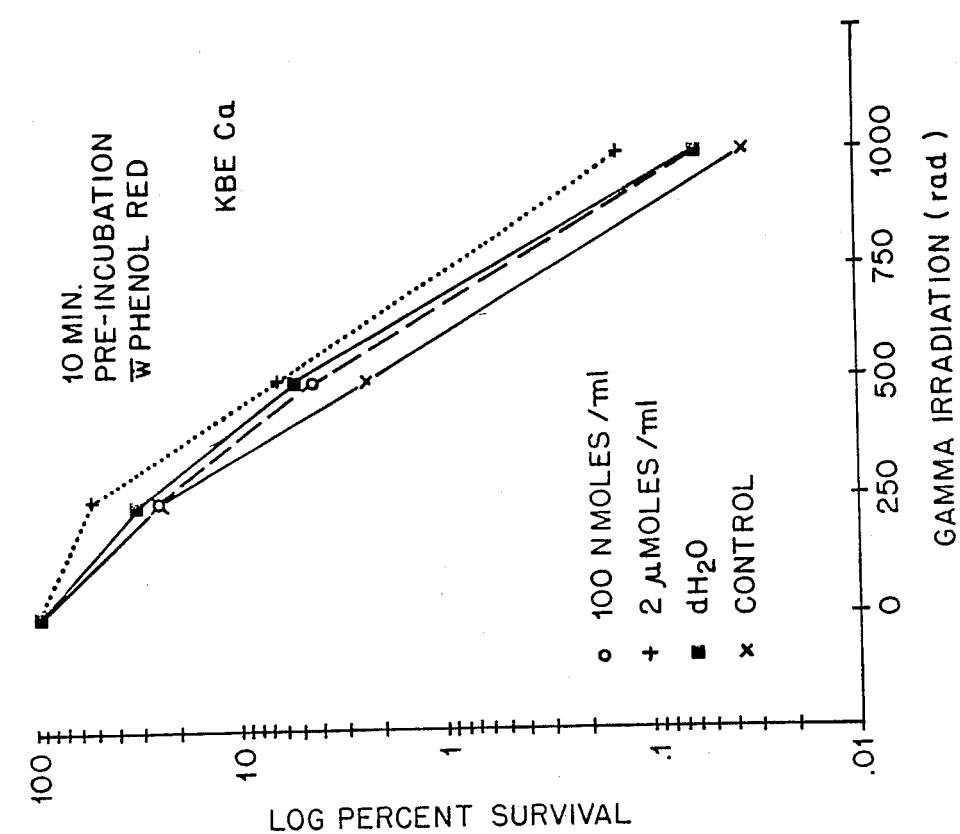

METHOD OF PREVENTION OF OXIDATIVE INJURY TO CELLS

STATEMENT OF GOVERNMENT INTEREST

The invention described herein may be manufactured and used by or for the Government for governmental purposes without the payment of any royalty thereon.

BACKGROUND OF THE INVENTION

The present application is a continuation-in-part application of my co-pending application Ser. No. 652,370, filed on Sept. 19, 1984, now U.S. Pat. No. 4,766,150 which is a divisional application of application Ser. No. 251,694, filed on Apr. 7, 1981, now U.S. Pat. No. 4,486,408.

This invention relates to a process for protecting animal cells from oxidative injury such as that caused by exposure to chemical, biochemical, or physical metabolic stressors or from inborn deficiencies in antioxidative biochemical pathways which increase cell sensitivity to oxidation induced by such chemical and/or physical factors.

This invention further relates to a process for suppressing the immune-system of animals wherein an immunosuppressive amount of 3-aminotyrosine is administered to an animal to suppress that animal's endogenous immune system.

There is a relationship between nonphosphorylating oxidative metabolism (membrane peroxidation) and immune cell activation. The production of peroxides and other active oxidants is one of the earliest measurable signals of immunogenic stimulation. Wrogemann, K., et al., 8 Eur. J. Immunol. 749–752 (1978); Strauss, R. R., et al., 15 Infect. Imm. 197–203 (1977). The antibacterial and antiparasitic activities of neutrophils (Clark, R. A. and S. J. Klebanoff, "Studies on the mechanism of antibody-dependent polymorphonuclear leukocyte-mediated cytotoxicity," 119 Journal of Immunology 1413–1418 (1977)) and eosinophils (DeChatelet, L. R., et. al., "Oxidative metabolism of the human eosinophil," 50 Blood 525–535 (1977)) are associated with peroxidative activity. Furthermore, peroxidative activity is not only associated with killing of target cells by leukocytes such as macrophages but also with cell differentiation of macrophages themselves and other cell types with which they interact.

The activators of oxidative metabolism (lipopolysaccharide and Bacille Calmette-Guerin, see Johnston, R. B. and S. Kitagawa, "Molecular basis for the enhanced respiratory burst of activated macrophages," 44 Federation Proceedings 2927–2932 (1985)) also induce tumor necrosing factor, or cachectin (see Old, L. J., "Tumor necrosing factor (TNF)," 230 Science 630–632 (1985)), and interleukin 1 (Prestidge, R. L., et. al., "Interleukin 1: Production by P388D$_1$ cells attached to microcarrier beads," 46 Journal of Immunological Methods 197–204 (1981)). Tumor necrosing factor not only attacks tumor cells but also mediates the effects of endotoxin and the cachexia (lipolytic activity) of severe chronic infections and cancer. Interleukin 1 is necessary for committing T cells to proliferation in response to specific antigens and recruiting other lymphocytes to specific cellular or humoral responses. The latter effect is mediated by T cell production of interleukin 2.

The activation of oxidative metabolism of leukocytes is not always beneficial or innocuous. Excessive peroxidation may inhibit lymphocyte functions. Fischman, C. M., et. al., "Inhibition of lectin-induced lymphocyte activation by 2-cyclohexene-1-one: Decreased intercellular glutathione inhibits an early event in the activation sequence." 127 Journal of Immunology 2257–2262 (1981). Furthermore, excessive perixidation may activate mast cells and, subsequently, allergic reactions. Ohmori, H., et. al., "Xanthine oxidase-induced histamine release from isolated rat peritoneal mast cells: Involvement of hydrogen peroxide," 28 Biochemical Pharmacology 333–334 (1979). Autoxidation of red blood cells initiated by inflammation or chemical or physical insult may lead to autoimmune responses. Low, P. S., et. al., "The role of hemoglobin denaturation and Band 3 clustering in red blood cell aging." 227 Science 531–533 (1985).

Physical stressors that enhance peroxidation mimicking the effects of inflammation (leukocyte production of active oxygen species) include ionizing radiation and hyperthermia. It is well known that ionizing radiation of medium containing water and oxygen (i.e., tissue) produces peroxide and free radicals. Casarett, A. P. Radiation Biology, Englewood, N.J.: Prentice-Hall, Inc. (1968), Chapter 4). Phenols can act as co-oxidants forming stable phenolic free radicals. Phenol red, a commonly used pH indicator in tissue culture media, can interact with oxygen free radicals formed in vitro ionizing radiation experiments. The phenolic free radicals may, in turn, interact with other oxidizable substrates. Also, hyperthermia of red blood cells can yield superoxide and peroxide. Kiel, J. L., and D. N. Erwin, "Thermochemiluminescent assay of porcine, rat, and human erythrocytes for antioxidative deficiencies," 143 Analytical Biochemistry 231–236 (1984); Kiel, J. L. and D. N. Erwin, "Microwave and thermal interactions with oxidative hemolysis," 16 Physiological Chemistry and Physics and NMR 317–323 (1984). The peroxidative reactions associated with inflammation, ionizing radiation, and hyperthermia may result in membrane protein crosslinking (Karel, M., "Lipid oxidation, secondary reactions, and water activity of foods." In M. G. Simic and M. Karel (eds.), Autoxidation in Food and Biological Systems, pp. 191–206, New York: Plenum Press (1980)), cell lysis (Lynch, R. E., and I. Fridovich, "Effects of superoxide on the erythrocyte membrane," 253 Journal of Biological Chemistry 1838–1845 (1978)), oxidation of proteins or enzymes with loss of function (Karel, M., supra), nicking DNA (Lown, J. W., S. K. and Sim, "The mechanism of the bleomycin induced cleavage of DNA," 77 Biochemical and Biophysical Research Communications 1150–1157 (1977)), and inhibition or activation of inflammation by the specific production of prostaglandins or leukotrienes (Goldstein, I. M., et. al., "Thromboxane generation by human peripheral blood polymorphonuclear leukocytes," 148 Journal of Experimental Medicine 787–792 (1978); Weissman, G., et. al., "Prostaglandins and inflammation: receptor/cyclase coupling as a explanation of why PGE's and PGI$_2$ inhibit functions of inflammatory cells," 8 Advances in Prostaglandin and Thromboxane Research 1637–1654 (1980); Samuelsson, B., et al., "Introduction of a nomenclature: Leukotrienes," 17 Prostaglandins 785–787 (1979); and Zurier, R. B. and G. Weissman, "Effect of prostaglandins upon enzyme release from lysosomes and experimental arthritis," In P. W. Ramwell and B. B. Phariss (eds.) Prostaglandins in Cellular Biology, pp. 151–172, New York: Plenum Press (1972)).

Therefore, any inhibitor of early peroxidative events would serve as a profound immunomodulator and anti-inflammatory agent. Dose-dependent effects of such inhibitors are expected; that is, protection without inhibition of the immune response at low doses and immunosuppression at high doses. Also, other tissues affected by autoxidation and peroxidation (i.e., red blood cells) would be protected by such an inhibitor.

As noted above, the autoxidation of red blood cells (RBCs), which may be initiated by such stimuli as inflammation or chemical or physical insult, may lead to autoimmune responses. However, the autoxidation of RBCs is a common occurrence even under normal conditions. In other words, such stimuli are not required to initiate autoxidation. As much as 3% of the total hemoglobin (the hemoglobin being contained within the RBCs) is converted to methemoglobin each day, an event which results in the formation of superoxide, hydrogen peroxide, and lipid peroxides, all of which are oxidants which pose a significant threat to all cells, but especially the RBCs, where the event occurs.

Under normal circumstances, the oxidants generated during autoxidation cause little damage to the RBCs due to the scavenging action of several enzymes. These enzymes include superoxide dismutase, which catalyzes the conversion of superoxide to hydrogen peroxide and molecular oxygen, and catalase and peroxidase, which catalyze the conversion of hydrogen peroxide to water in the presence of available electrons. The peroxidase involved in autoxidative pathways, at least in known mammalian cells, is glutathione peroxidase, which is a selenium-containing enzyme that oxidizes reduced glutathione and reduces peroxides.

Inherited deficiencies of superoxide dismutase and catalase, or deficiencies in key co-enzymes, may lead to increased susceptibility to oxyhemoglobin autoxidation, as may the inhibition of those enzymes. Shanus, supra; Metzler, D. E., *Biochemistry: The Chemical Reactions of Living Cells*, New York: Academic Press (1977), pp. 564–565. Disorders such as malignant hyperthermia have been associated with inherent glutathione peroxidase deficiency in swine. Schanus, E. G., et al., "Malignant hyperthermia (MH): Porcine erythrocyte damage from oxidation and glutathione peroxidase deficiency," in G. J. Brewer (ed.), *The Red Cell, Fifth Ann Arbor Conference*, New York: Alan R. Liss, Inc. (1981), pp. 323–336. The addition of various anionic nucleophiles (i.e., azides, halides and thiocyanate) to the cells accelerates the autoxidation reaction. Wallace W. J., et al., "The mechanisms of hemoglobin autoxidation: Evidence for proton-assisted nucleophilic displacement of superoxide of anions", 57 Biochem. Biophys. Res. Comm. 1104–1109 (1974). Increasing the temperature to which the cells are exposed by 3° C. doubles the rate of oxyhemoglobin autoxidation under physiological conditions. Wallace, W. J. et al., "A role for chloride in the autoxidation of hemoglobin under conditions similar to those in erythrocytes." 43 FEBS Letters 33–36 (1974).

Further, ample evidence has shown that the combination of certain peroxidases with hydrogen peroxide and a halide ion produces a system with strong cytotoxic properties. The myeloperoxidase-hydrogen peroxide-chloride system forms a potent cytotoxic system effective against bacteria, fungi, viruses, mycoplasma, and various mammalian cells. Similarly, the lactoperoxidase-hydrogen peroxide-thiocyanate system and the horseradish peroxidase-hydrogen peroxide-chloride system have been shown to have potent cytotoxic activities.

An equally cytotoxic system is obtained when instead of hydrogen peroxide, a hydrogen peroxide generating system is used. Thus, the glucose oxidase-horseradish peroxidasechloride combination yields a potent cytotoxic system upon the addition of glucose. Galactose oxidase and xanthine oxidase have also been shown to be effective in this respect. Furthermore, we showed that the endogenous NADH oxidase activity of horseradish peroxidase is also capable of promoting the cytotoxic activity of the enzyme in the presence of chloride ions.

A large body of evidence indicates that cytotoxic systems such as those described above may be operative in polymorphonuclear leukocytes, eosinophils, macrophages, and other cell types with cytotoxic properties. Such cells in general appear to utilize an NADH or NADPH oxidase as the peroxide-generating enzyme.

Macrophages are a necessary component in the augmentation of natural killer cell activity by Bacillus Calmette-Guerin (BCG) in mice. BCG also increases the peroxide and superoxide production by macrophages. The possibility thus exists that the peroxidase system of the macrophages plays a role in the augmentation of the natural killer cell activity. Similarly, peripheral lymphocytes, which are predominantly T-cells, contain a cytotoxic peroxidase. Chemiluminescence resulting from peroxide generating oxidative metabolism is observed when T lymphocytes are stimulated by concanavalin A. Furthermore, immunization of mice with either soluble or particulate antigens causes an increase in peroxidase activity in the spleen which precedes the generation of specific antibody. These observations suggest that oxidase and/or peroxidase activity is in some way involved in developing specific immune responses.

Thus far none of the cytotoxic systems described above have been used in any in vivo experiments. However, some relevant experiments were done some time ago by Schultz and his colleagues. Schultz, Snyder, Wer, Berger and Bonner, "Chemical Nature and Biological Activity of Myeloperoxidase," in *Molecular Basis of Electron Transport*, New York: Academic Press, (1972), pp. 301–321 (1972); Schultz, Baker, and Tucker, "Myeloperoxidase-Enzyme-Therapy of Rat Mammary Tumors," in *Cancer Enzymology*, New York: Academic Press (1976), pp. 319–334 (1976). Using mice bearing 20-methylcholanthrene induced tumors, these authors injected myeloperoxidase in combination with thio-TEPA, an antitumor drug. They observed a significant reduction in tumor growth in the treated mice, but no complete remissions. Neither myeloperoxidase nor thio-TEPA alone were effective in reducing tumor growth. The inhibition of tumor growth lasted as long as the treatment with myeloperoxidase and thio-TEPA was continued.

These results indicated that the activity of myeloperoxidase could play a role in the control of tumor growth, either directly or indirectly. Definite conclusions are difficult to obtain with such experiments, however, because the biological half-life of myeloperoxidase is only about 24 hours. It is noteworthy that the toxic activity appeared to be specifically directed to the tumor tissue.

SUMMARY OF THE INVENTION

We have discovered that several peroxidases, when used in combination with a hydrogen peroxide and/or superoxide generating system, possess a potent cytotoxic activity toward prokaryotic and eukaryotic cells when administered to tumor-bearing animals. We further discovered that this cytotoxic activity appears to be exclusively directed toward the neoplastic tissues.

In order to obtain the tumoricidal activity, it is necessary that the two enzymes be kept in close proximity to each other and that the enzymes be stabilized such as to significantly increase their in vivo half-life. Both these requirements can be met by immobilizing the enzymes, either separately or in combination, onto an insoluble support. This immobilization can be done by either chemically attaching the enzyme molecules onto the insoluble support or by entrapment of the enzyme molecules within the molecular matrix of the support.

For the purpose of this patent application, immobilization is defined as the association of active protein molecules with an insoluble macromolecule by any means that prevents the protein molecules from moving away from the insoluble support.

An insoluble compound is defined as a compound that does not form a true solution in an aqueous medium at around physiological pH values; aqueous media being aqueous buffer media as well as any bodily fluids. Compounds that form colloidal solutions in the above mentioned aqueous media are considered to be insoluble compounds.

One or more injections of the immobilized enzyme conjugate described above into tumor-bearing animals results in a partial or total regression of the tumor tissue. It is preferable that the material be injected into the tumor or proximal to the tumor; however, primary tumors as well as metastasized tumors are subject to the cytotoxic action of the immobilized enzymes.

We further discovered that the immobilized enzyme systems act as potent activators of the specific immune response in tumor-bearing animals. This activation of the specific immune response therefore may all or in part be responsible for the regression of the tumors. Similarly, injection of potent inhibitors, namely 3-Aminotyrosine, of the cytotoxic activity of the immobilized enzyme system results in a depression of the specific immune response and makes animals more susceptible to develop tumor growth. These inhibitors also inhibit, prevent or reduce the cytotoxic effects of such stimuli as physical or chemical stimuli or inflammatory reactions which result in the formation of oxidants such as peroxide which cause injury to the cells or tissue of living animals.

It is, therefore, an object of this invention to prevent damage to normal cells and/or tissue, either on a gross or microscopic level.

It is a further object of this invention to provide a process for suppressing the immune system of animals by administering an immunosuppressive amount of 3-aminotyrosine to an animal.

It is a further object of this invention to prevent oxidative injury to the cells of a living organism by administering 3-aminotyrosine or a derivative thereof to that organism.

It is another object of this invention to provide a method of counteracting the antioxidative effects of the exposure of living cells to metabolic stressors which effect the generation of oxidants by those cells.

It is another object of this invention to provide a method of decreasing the damage to living cells caused by thermal insult.

Yet another object of the present invention is to reduce the injury caused to cells by the oxidative effects of inflammation reactions by administering an anti-inflammatory amount of 3-aminotyrosine or a derivative thereof to an animal to suppress that inflammatory reaction.

It is another object of this invention to provide a process for reducing the oxidative injury to cells caused by exposure of those cells to elevated temperatures.

It is another object of this invention to provide a method of decreasing the damage to living cells caused by exposure to autoxidizable drugs.

It is another object of this invention to provide a method of decreasing the damage to living cells caused by exposure of those cells to certain toxic substances.

It is another object of this invention to provide a method of decreasing the damage to living cells caused by exposure of those cells to ionizing or other radiation.

These objects of this invention, as well as other objects related thereto, will become apparent from a consideration of the following description of the invention.

BRIEF DESCRIPTION OF THE DRAWINGS

FIG. 3 is a graph showing the log percent survival of L5178Y murine lymphosarcoma cells as a function of gamma irradiation dosage with no pre-incubation in 100 nanomoles/ml (—0—) and 2 micromoles/ml (...+...) solutions of 3-aminotyrosine before exposure to dosages of 0, 250, 500 and 1000 rads (✶=control).

FIG. 4 is a graph showing the log percent survival of L5178Y murine lymphosarcoma cells as a function of gamma irradiation dosage after 16 hours of incubation in 100 nanomoles/ml (...+...) and 2 micromoles/ml (—0—) solutions of 3-aminotyrosine at dosages of 0, 250, 500 and 1000 rads (✶=control).

FIG. 5 is a graph showing the log percent survival of human KBE epidermoid carcinoma cells as a function of gamma irradiation dosage with no pre-incubation in 100 nanomoles/ml (—0—) and 2 micromoles/ml (...+...) solutions of 3-aminotyrosine before exposure to the radiation at dosage levels of 0, 250, 500 and 1000 rads (■=distilled water; ✶=control).

FIG. 6 is a graph showing the log percent survival of human KBE epidermoid carcinoma cells grown on media containing phenol red as a function of gamma irradiation dosage after 24 hours of incubation in 100 nanomoles/ml (—0—) and 2 micromoles/ml (...+...) solutions of 3-aminotryrosine at dosages of 0, 250, 500 and 1000 rads (■=control).

DETAILED DESCRIPTION OF THE INVENTION

The present invention resulted from the discovery that 3-aminotyrosine inhibited the action of the potent antitumor agent formed by the cross-linking of an oxidase and a peroxidase and the immobilization of those cross-linked enzymes. Upon further inquiry, it was discovered that 3-aminotyrosine appeared to inhibit the action of that anti-tumor agent by suppressing the immune system. Those studies are described below.

Further inquiry into the mode of action of 3-aminotyrosine indicates that the immunosuppressive effect of 3-aminotyrosine apparently results from its antiperoxidative action, i.e., it inhibits the action of peroxidative enzymes. As noted above, there is considerable evidence of a relationship between peroxidation and immune cell activation. In fact, it has now been discovered that 3-aminotyrosine and derivatives thereof are effective anti-inflammatory agents.

It has further been discovered that the antiperoxidative effect of 3-aminotyrosine and derivatives thereof is instrumental in the use of 3-aminotyrosine and derivatives thereof to affect any metabolic process which involves peroxidation; in particular, to prevent or reduce the injury to living cells caused by the production of oxidants during that metabolic process. This oxidative injury can be caused by a number of stimuli (summarized above), for instance, inflammation reactions, thermal insult, exposure to ionizing radiation, exposure to certain toxic chemicals or exposure to certain drugs. Examples are presented below demonstrating the ability of 3-aminotyrosine and derivatives thereof to protect against peroxidative injury from such stimuli. The 3-aminotyrosine can be present relative to the mammalian cells in a range of 74 nanomoles to 2 millimoles per milliliter of cells and in an intermediate amount of 74 nanomoles to 1.44 micromoles.

Figure 1:
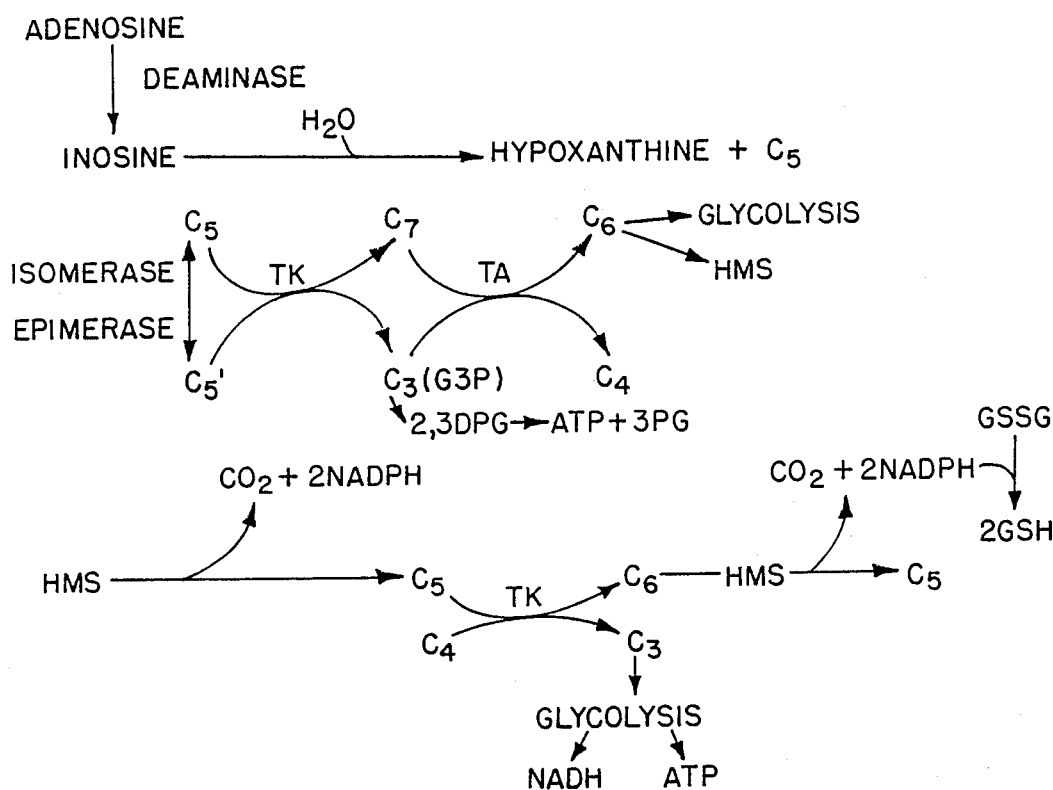
FIG. 1 is a schematic presentation of the metabolic pathways which control the autoxidation of red blood cells (Hb=hemoglobin; $HbO_2$=oxyhemoglobin; MetHb=metheglobin; SOD=superoxide dismutase; GSH=reduced glutathione; G-S-S-G=oxidized glutathione; G-6-P=glucose-6-phosphate; UFA=unsaturated fatty acids).
Figure 2:
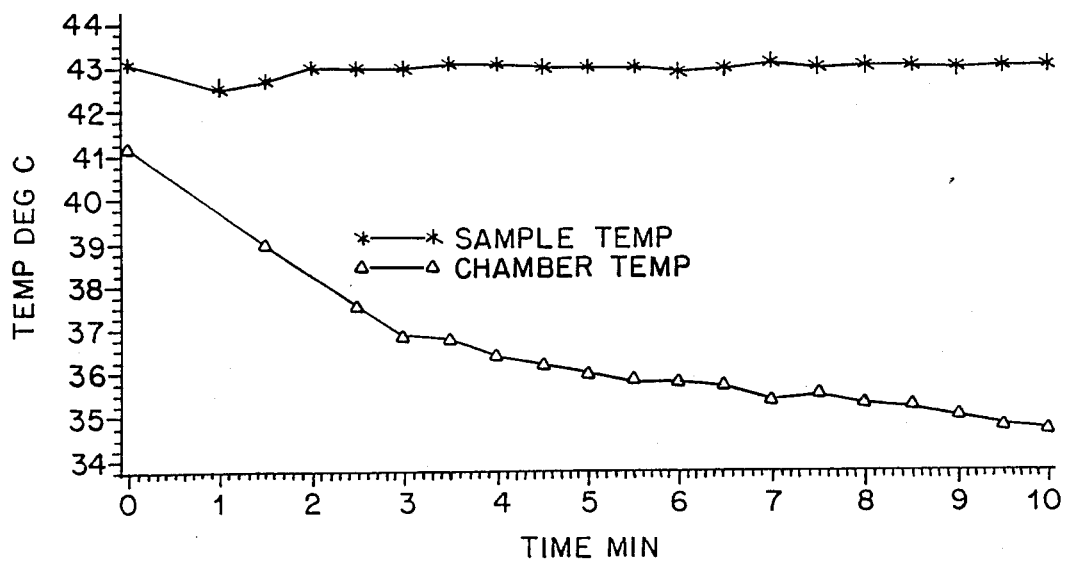
FIG. 2 is a graph of temperature (in degrees centigrade) as a function of time (in minutes) showing the temperature measurements made in the microwave radiation (2450 MHz) exposure device within the RBC sample (stars) and the air chamber enclosing the sample (open triangles) during irradiation (average SAR was 91±4 W/kg) of the sample.

Also as noted above, autoxidative metabolic processes are constantly generating oxidants such as hydrogen peroxide and superoxide, even in the normal cell. FIG. 1 summarizes the metabolic pathways which control the autoxidation of red blood cells. There are many clinical disorders which involve a breakdown at some point in these metabolic pathways. For instance, as a result of a nutritional or genetic deficiencies or exposure to toxic chemicals or autoxidizable drugs, an individual may have deficiencies in endogenous levels of catalase, superoxide dismutase or the other enzymes or necessary co-factors involved in the metabolic pathways summarized in FIG. 1. Such an individual may be particularly sensitive to certain stimuli such as high temperatures, inflammation reactions or certain autoxidizable drugs. The later is of particular concern because of the many beneficial therapeutic uses of certain autoxidizable drugs. 3-Aminotyrosine and derivatives thereof may, therefore, be given to effectively counteract or offset the oxidative effects of those autoxidizable drugs, allowing those drugs to be used successfully in those individuals for therapy. 3-Aminotyrosine and derivatives thereof will counteract the oxidative effects of the following autoxidizable drugs:

---

Toxins
Paraquat
Anesthetics
Halothane
Analgesics
Acetanilid
Acetophenetidin (phenacetin)
Acetylsalicylic acid
Acetaminophen
Anticonvulsants
Phenytoin
Phenacemide
Phenobarbitol
Carbamazepine
Mephenytoin
Anorectics
Chlorphentermine
Sulfonamides and Sulfones
Sulfanilamide
Sulfapyridine
Diaphenylsulfone
Thiazolsulfone
N—acetylsulfanilamide
Salicylazosulfapyridine (Azulfadine)
Sulfacetamide
Sulfamethozypyridazine (Kynex)
Antimalarials
Primaquine
Pamaquine
Pentaquine
Quinocide
Quinacrine (Atabrine)
Non-Sulfonamide Antibacterial Agents
Furazolidine
Furmethanol
Nitrofurantoin (Furadantin)
Nitrofurazone
Chloramphenicol
Aminoglycoside antibiotics,
 i.e., Streptomycin, Gentomicin,
Tobramycin
Metronidazole (Flagyl)
Miscellaneous
Napthalene
Trinitrotoluene
Methylene blue
Naldixic acid
Phenylhydrazine
Quinine
Quinidine
Ascorbic acid
Niridazole

---

As a matter of convenience to the reader, the insoluble cross-linked cytotoxic oxidase-peroxidase system of the present invention will be referred to as "ICCOPS". Further, the phrase "3-aminotyrosine and derivatives thereof" refers to those substances which are capable of prevention and/or moderation of oxidative damage to living cells when those cells are exposed to the various metabolic, chemical and physical stressors described herein. In particular, the phrase "3-aminotyrosine and derivatives thereof" includes, but is not limited to, the following substances which also act as peroxidative inhibitors:

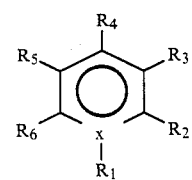

Where $R_1$ can be an amino acid ester, an amino acid amide, an amine (primary, secondary, tertiary or quarternary), a carboxylic acid, or an α-keto-carboxylic acid. $R_2$, $R_3$, $R_4$, $R_5$, or $R_6$ can be amino, hydroxyl, or imino groups, or any combination of these substituents. The x can be either carbon or nitrogen. In a preferred derivative, at least one of the $R_2$, $R_3$, $R_4$, $R_5$ or $R_6$ substituents is an amino group.

In the following detailed description, to induce tumors for the purpose of verifying the efficacy of the method of the present invention, three to four-week-old Sprague-Dawley rats were each injected intraperitoneally with 0.5 or 1.0 ml of Novikoff hepatoma suspension. The tumors were allowed to develop for five days or until ascites was evident. At this time, some animals were sacrificed to establish the presence of tumor. The remaining tumor-bearing animals were then divided into test and control groups and treatment was initiated. Some animals treated with ICCOPS were selected for additional treatment with 3-amino-L-tyrosine. Also, other rats, resistant to Novikoff hepatocarcinoma, were treated with 3-amino-L-tyrosine.

PREPARATION OF ICCOPS

The cross-linked enzyme was prepared by dissolving 10 mg of horseradish peroxidase and 300 mg of bovine serum albumin or human serum albumin in a solution containing 2 ml glucose oxidase (2400 units) and 2.5 ml of 0.1M phosphate buffer, pH 6.9. Polymerization was initiated by adding 75 μl of 25% glutaraldehyde, a polymerizing agent, to the enzyme solution. The mixture was incubated for at least 24 hours at 4° C. or until a gel was formed. The gel was soaked in 100 times its volume of distilled water. The water was decanted off and the gel was further washed with 100 more volumes of distilled water over a sintered glass filter. The gel was then frozen and lyophilized. The lyophilized gel was ground in a mortar with a pestle to a size that would pass through an 18 gauge hypodermic needle when swollen in phosphate buffered saline (PBS), pH 7.4. The powdered ICCOPS was stored at −20° C. until used.

PEROXIDASE ACTIVITY OF IMMOBILIZED ENZYME

Oxidase and peroxidase activity was qualitatively determined by adding 1 mg of the immobilized enzyme system to 0.1% glucose in PBS, pH 7.4, containing 1.5 mg ABTS per ml. If the green solution turned blue within an hour, the oxidase and peroxidase were considered active.

PROCEDURES FOR TREATMENTS OF TUMOR-BEARING RATS

The basic procedure for treatment with ICCOPS required three consecutive days of treatment with 5 mg of the preparation suspended in 1 ml PBS, pH 7.4, containing 0.1% glucose. The suspension was injected into the abdominal cavity of rats bearing 5-day old tumors. Variations in the treatment regimens were used as indicated in the results which are described later herein.

ASSAY OF THE CELLULAR IMMUNOLOGICAL RESPONSE IN RATS

A single-cell suspension was produced from the spleens by passage through a stainless-steel screen (Collector, Bellco Glass Co., Vineland, New Jersey). The cells were washed once in Hank's Balanced Salt Solution (HBSS, Colorado Serum Co., Denver, Colorado), and then suspended in a Tris-ammonium chloride solution. The Tris-ammonium chloride solution was prepared from 10 ml 0.17M Tris and 90 ml 0.16M ammonium chloride and the solution was adjusted to pH 7.2. The suspension was incubated in a water bath at 37° C. to lyse the erythrocytes. The cells were centrifuged at 1000 rpm in a CRC 5000 DAMON/IEC Division centrifuge for ten minutes and the supernatant was discarded. The cells were washed in HBSS and again centrifuged. The pellet was suspended in Modified Eagles Medium (Gibco, Grand Island, New York) supplemented with 10% (V/V) normal rabbit serum (KC Biologicals, Linexa, Kansas), Hepes buffer 2 micromoles/ml (Gibco), non-essential amino acids (Gibco) and penicillin-streptomycin. A 100 μl aliquot of cells was withdrawn and mixed with 100 μl 0.4% trypan blue. After three minutes, the cells and dye mixture were diluted with 19.8 ml physiological saline solution—resulting in a 1:200 dilution of cells. The cells were counted in a hemocytometer and their concentration adjusted to $2 \times 10^6$ viable cells/ml. Viability was routinely greater than 90%.

The various antigens and mitogens were stored sterile at 4° C. dissolved in PBS, pH 7.2, at concentrations of 1 mg/ml, 100 μg/ml, and 10 μg/ml. Cultures were performed in standard 96-well microtiter plates constructed from tissue-culture quality plastic (Falcon Plastics, Los Angeles, California). To the wells requiring antigen at 1 μg/ml, 10 μl of antigen at 10 μg/ml was added. To achieve final concentrations of 10 μg/ml or 100 μg/ml, for example, 10 μl of 100 μg/ml or 1 mg/ml were added, respectively. Other concentrations of various mitogens were prepared in a similar manner. The specific antigen utilized was Keyhole Limpet Hemocyanin (KLH, Schwartz/Mann Laboratories, Orangeburg, New York) with which the rats were inoculated subcutaneously 14 days prior to the introduction of tumor cells. Each rat received 200 μg of KLH in 0.1 ml PBS, pH 7.6. Concanavalin A (ConA) from Boehringer Mannheim (Indianapolis, Indiana) was the mitogen utilized in the assays. The negative control consisted of the addition of 10 μl of PBS at pH 7.2 to each control well. After the addition of antigen or mitogen, each well received 100 μl of the cell suspension. The plates were incubated at 37° C. in a humid atmosphere containing 5% $CO_2$ for 24 hours. Next, the wells were pulsed with 100 μl of MEM containing tritiated-thymidine at 5 μCi/ml, specific activity 2 Ci/mmol. After 48 hours of culture, the cells were harvested onto glass-fiber filters using a Titertech cell harvester (Flow Laboratories, McLean, Virginia). After drying, the filters were counted in a scintillation fluid consisting of toluene, PPO, and POPOP.

SOURCE OF RED BLOOD CELLS

Blood was collected from Landrace-Duroc swine from a closed herd. Pigs from this herd had previously expressed episodes of porcine stress syndrome (malignant hyperthermia) following halothane anesthesia. The blood was collected into acidic citrated dextrose solution in standard blood bags. The blood was diluted 1:10 in phosphate (0.1M) buffered saline (PBS), pH 7.4, in 10 ml aliquots, centrifuged in a clinical centrifuge, and the erythrocytes were resuspended in fresh PBS. The cells were stored at 4° C. until used in the various assays. The post-collection chronological age of the RBCs used for a particular assay is noted in the results for each assay. The cells were counted in an automated cell counter (Coulter ZBI, Coulter Electronics, Inc., Hialeah, Fla. 33010).

HEATING

Red blood cells were heated in 1 or 1.5 ml aliquots of PBS pH 7.4 with or without additional reagents in cellulose nitrate or polypropylene centrifuge tubes. Two concentrations of cells were used as indicated in the results. Heating was accomplished by three methods: microwave radiation, hot air, or water bath heating. The microwave device was a circularly polarized waveguide powered by a 1-kw S-band (microwave) amplifier (Model 10704,MCL, Inc., La Grange, Ill.). The heating of the sample at a specific absorption rate (SAR) of $91\pm4$ W/kg (continuous wave (CW), 2450MHz) was offset by an air-cooling system that maintained a constant temperature. This system has been previously described in greater detail in Kiel, J. L. and D. N. Erwin, "Microwave and thermal interactions with oxidative hemolysis", 16 Physiol. Chem. Phys. Med. NMR, 317-323 (1984), which reference is hereby incorporated in its entirety by this specific reference thereto. FIG. 1 shows the temperature control over time for 43° C. The temperature was held within $\pm0.2°$ C. by this system. In the absence of microwave radiation, the temperature was held constant by hot air alone. The microwave/hot air system was brought to 37° C. for 15 min. prior to raising the temperature to 43° C. by microwaves or hot hot air. The water bath heating held the temperature within $\pm0.5°$ C. Heating times were 10, 15, or 30 min. The temperatures examined were 37°, 43°, 45°, or 48°.

THERMAL FRAGILITY

Hemoglobin released into the supernatants of the heated cells were determined by the method described in the above-incorporated reference of Kiel and Erwin (1984). In brief, the supernatants were collected following centrifugation in a clinical centrifuge, diluted 1:2 in PBS, pH 7.4, and the optical absorbances at 410 nm were determined in a dual beam spectrophotometer. Pyruvate, lactate, inosine, hydrogen peroxide, mimosine, and/or 3-amino-L-tyrosine were added to the samples as indicated in Tables 1-3 and 9-12. All reagents were diluted in PBS and the final volumes of the samples were constant.

PREPARATION OF CONCANAVALIN A-LUMINOL-BOVINE SERUM ALBUMIN CONJUGATE

The luminol-bovine serum albumin (Lu-BSA) complex was made by mixing 2 mg luminol (5-amino-2, 3-dihydrophthalazine-1,4-dione), 0.2 ml of 2 mg BSA/ml PBS (pH 6.9), and 1.6 ml of PBS, pH 6.9. The preparation was then passed through a 0.22 μm nitrocellulose filter to remove insoluble luminol. Next, 0.2 ml of 2 mg Con A/ml of PBS, pH 6.9, was added to the filtrate. After gentle mixing, 10 μl of 25% glutaraldehyde were added. The solution was incubated in the refrigerator for 1 hour. To stop the conjugation, 100 mg of glycine was added to the solution. The solution was then pressed through a 48 ml column of dextran gel filtration beads equilibrated with PBS, pH 6.9. The gel exclusion size was greater than 5000 for globular molecules. The fractions were collected and tested for luminescent labeling activity.

USING CONCANAVALIN A-LUMINOL-BOVINE SERUM ALBUMIN CONJUGATE

One ml of supernatant of each 10 ml aliquot of 1:20 diluted RBCs was replaced with 1 ml of Con A-Lu-BSA solution as previously described. The preparation was incubated for 15 min. at 37° C. in a water-jacketed cell culture incubator. The cells were then pelleted in a clinical centrifuge, resuspended in PBS, and washed in the same manner two additional times. The washed cells were maintained at 4° C. until used the same day of preparation.

Following exposure to chemical or physical stressors, 100 μl of the RBC suspension was added to 500 μl of PBS, pH 7.4, containing 0.3% hydrogen peroxide, in a scintillation vial. To activate the sample, 100 μl of 0.1N NaOH were added to the vial in place in an ATP photometer (Integrating ATP Photometer Model 3000, Science Applications, San Diego, California 92121) The photometer was set to a dark count of 1 count/30 second at a sensitivity of 600 at room temperature (approximately 23° C.). All counts followed a 5 second delay period to allow for stabilization of the photomultiplier. The counts are reported as counts/30 sec.

MEASURING LUMINOL-BOVINE SERUM ALBUMIN BINDING

Nonspecific binding of Lu-BSA to porcine RBCs was measured following treatment with hydrogen peroxide, pyruvate, and/or 3-amino-L-tyrosine at 4°, 37°, or 45° C. The exposure times for those agents were 15 min, 30 min, or 72 hours. The reagents were removed by centrifugation. Three binding protocols were followed: (1) 0.25 ml of 1:20 RBCs (19 days post collection) were incubated with 0.25 ml of 1 mg/ml Lu-BSA in PBS, pH 6.9, for 30 min at 37° C. and washed (Table 1); (2) 0.05 ml of packed RBCs (less than 24 hours post collection) were resuspended in 0.2 ml of the Lu-BSA solution and incubated overnight at 4° C. (Table 2); and (3) 0.05 ml of packed RBCs (72 hours post collection) were resuspended in 0.2 ml of Lu-BSA solution and incubated at 37° C. for 30 min (Table 3). The cells in all three protocols were washed once in PBS, pH 7.4, and resuspended in PBS to final dilutions of 1:20 for (1) and 1:30 for (2) and (3). Following this preparation, 100 μl of each cell suspension were added to 500 μl of PBS, pH 7.4, in a scintillation vial. The vial was placed in the photometer and the solution was activated by the addition of 100 μl 0.1N NaOH. The settings for the photometer were as previously described for the Con A-Lu-BSA.

TABLE 1

| Pretreatment (37° C., 15 min) | CL (30 s) |
|---|---|
| Hydrogen peroxide (44 mM) | 558 ± 157 (4) |
| PBS (pH 7.4) | 68 ± 22 (4) |

TABLE 2

| Reagent | Temp. (30 min) | CL (30 s)* | Percent difference from control |
|---|---|---|---|
| None (control) | 4° C. | 380 ± 63 (4) | 0 |
| None | 37° C. | 583 ± 78 (4) | 53 |
| Hydrogen peroxide (11.7 mM) | 37° C. | 1346 ± 386 (4) | 254 |
| 3-Amino-L—tyrosine (1.49 mM) and hydrogen peroxide (11.7 mM) | 37° C. | 663 ± 145 (4) | 74 |
| None | 45° C. | 600 ± 110 (4) | 58 |

TABLE 2-continued

| Reagent | Temp. (30 min) | CL (30 s)* | Percent difference from control |
|---|---|---|---|
| Pyruvate (1.33 mM) | 45° C. | 1203 ± 266 (3) | 216 |
| 3-Amino-L—tyrosine (1.49 mM) | 45° C. | 550 ± 126 (4) | 45 |

*Cells without label had 5 ± 3 counts/30 s when base activated.

TABLE 3

| Reagent pretreatment | CL (counts/30 s) | Percent difference from control. |
|---|---|---|
| None (control) | 883 ± 129 (3) | 0 |
| 3-Amino-L—tyrosine (1.49 mM)* | 794 ± 156 (4) | −10 |
| Pyruvate (1.33 mM) | 2348 ± 646 (3) | 166 |
| 3-Amino-L—tyrosine (1.49 mM) and Pyruvate (1.33 mM) | 964 ± 230 (3) | 9 |

*Final concentration; preincubated at 4° C. for 72 h.

L5178Y MURINE LYMPHOSARCOMA CELLS

A. Addition of 3-Aminotyrosine Immediately Before Radiation Exposure

The L5178Y murine lymphosarcoma cell line is heterozygous at the thymidine kinase locus. The cells grow and are treated in suspension culture, and survival was determined using a colony formation assay in soft agar as described briefly below. The THMG/THG treatment described below was performed before each assay to purify the population of non-heterozyous cells. The details of the cell line and the cloning assay are given in Fischer, G. A. and A. C. Sartorelli, "Development, maintenance and assay of drug resistance," In H. N. Eisen (ed.) *Methods in Medical Research,* Vol. 10, Chicago: Yearbook Medical Publishers, Inc. (1964), pp. 247–262 and Clide, D., et al., "Validation and characterization of the L5178Y/TK+/− mouse lymphoma mutation assay system," 59Mutation Research 61–108 (1979).

L5178Y cells are regularly maintained in Fishers medium for leukemic cells of mice (GIBCO), supplemented with 10% heat-inactivated horse serum, penicillin/streptomycin at 50 units/ml and 50 μg/ml, respectively, pluronic acid at a final concentration of 0.1%, and sodium pyrurate at a final concentration of 0.1 mg/ml. This medium is designated "F10p". The L5178Y cell cycle time is 10 to 12 hours.

The cell density in a mass culture of thymidine hypoxanthine methotrexate glycine/thymidine hypoxanthine glycine (THMG/THG) treated L5178Y cells was determined by Coulter counter and the cells were diluted with fresh warm F10p medium to bring the cell density for treatment to 600,000 cells/ml. Volumes of 10 ml of cell suspension were distributed into three T-25 flasks, and 0.05 ml volumes of solutions of 3-aminotyrosine, as well as a 0.05 ml of distilled water used as a control, to provide a ratio of 5 microliters per 1 ml of cell suspension (a 1:200 dilution) in each flask. In these experiments, the cells were treated with chemical under reduced lighting, but not as totally light sensitive.

The cells were then reincubated for 10 minutes at 37° C. The flasks were then placed simultaneously in the chamber of the GammaCell 40 irradiator at room temperature. The dose rate for the Cesium-137 exposure was 121.6 rads/min. It has been determined that the temperature of water in a T-25 flask originally at 37° C. placed in the irradiation chamber decreases during an 8 min period to approximately 30° C. Flasks were removed after exposure of 0, 250 rads (2.5 Gy), 500 rads (5.0 Gy), and 1000 rads (10 Gy).

After the irradiation, the cells were centrifuged and the supernatant discarded. The cells were resuspended in F10p medium, and again centrifuged. The washing process was repeated and the cells were resuspended in 10 ml of complete medium and counted.

A growth curve study was performed in duplicate by initiating flasks with 60 ml of cell suspension at 20,000 cells per ml. The cells were incubated at 37° C. with continued rotation in 250 ml plastic Erlenmeyer flasks. The cell density was determined by Coulter counter on a daily basis over a 72 hour period.

The remainder of the cell suspension after irradiation was used for determination of survival by colony formation in soft agar. For each dose, based on estimated survival probability, different numbers of cells were distributed in soft agar suspension (0.4% DIFCO Noble Agar) into 100 mm petri dishes. The dishes were briefly chilled to gel the agar, and then after brief warming in the laminar flow hood, placed in the 37° C. humidified $CO_2$ incubator. The dishes were incubated for 11 days, and the number of colonies were determined using an Artek Automatic Colony Counter.

For the control and each 3-aminotyrosine and radiation dose, the percent cloning efficiency (% CE) was determined by dividing the number of colonies counted at 11 days by the number of cells seeded into the agar, times 100. The 0 dose % CE value was taken to be 100% survival for that chemical. The percent (%) survival reported was calculated by dividing the % CE after a given dose of radiation by the 0 dose % CE, times 100. The results are presented in graphical form in FIG. 3 and in tabular form in Table 4.

B. Pre-Incubation (16 hr) With 3-Aminotyrosine Prior to Irradiation

THMG/THG treated L5178Y cells were mass cultured and the cell density determined. Aliquots of the cell suspension with enough cells to give 300,000 cells per ml in 60 ml ($1.8 \times 10^7$ cells) were distributed into three 50 ml centrifuge tubes, and after centrifugation, the original growth medium was discarded. The cells were resuspended in GIBCO custom formulation medium which had been prepared without phenol red. The cells were then washed one more time by centrifugation and resuspended again in 10 ml of the phenol red-free medium. These 10 ml suspensions of cells containing $1.8 \times 10^7$ cells were then transferred into three flasks already containing 50 ml of phenol red-free medium, distilled water, and either 100 nanomoles/ml or 2 micromoles/ml solutions of 3-aminotyrosine. The exposure system was treated as light sensitive (i.e., procedures were performed under gold light or reduced lighting). The cells were then incubated in the dark at 37° C. for 16 hours. Immediately prior to the end of the 16 hours, the cell density was determined by Coulter counter.

At 16 hours, the cells were irradiated at 0, 250, 500, and 1000 rads as described above in the GammaCell irradiator at room temperature. Immediately after irradiation was completed, the cells were centrifuged, washed twice with F10p, and resuspended in 10 ml of F10p. The cell density was again determined by Coulter counter. Growth curve determinations with initial seeding at 20,000 cells per ml were performed for 72 hours as described above. Cell survival assay by soft agar colony formation was performed as described above, using 0.22% BBL agar (BBL Microbiology Systems) in place of the DIFCO agar previously employed. After 11 days incubation at 37° C., colonies were counted and cell survival was determined. The results are presented in FIG. 4 and Table 4.

KBE EPIDERMOID CARCINOMA CELL STUDIES

KBE Epidermoid carcinoma cells were seeded into 12 T-25 flasks at 150,000 cells per flask if the cells were to be incubated with 3-aminotyrosine for 24 hours prior to irradiation, or at 300,000 cells per flask if the cells were to be irradiated shortly after addition of 3-aminotyrosine. The cells were incubated for 19 to 24 hours to allow for attachment and achievement of rapid proliferation. For attachment and growth, Earle's BME medium (GIBCO 420-1300) with 10% fetal calf serum (GIBCO 240-6290), 50 units penicillin/ml and 50 micrograms/ml streptomycin (GIBCO 600-5140) and 25 mM HEPES buffer (SIGMA) were employed. In those experiments performed with media containing phenol red, this medium was replaced (in

TABLE 4

Ratios of Final to Initial Cell Density in Growth Curve Experiment and Ratios of Percent Survival In Soft Agar Assay - L5178Y Murine Lymphosarcoma Cells A. Zero Hour Incubation: Final Cell Density/Initial Cell Density[1]

| Dose (rads) | Control | 100 nanomoles/ml 3-Aminotyrosine | 2 micromoles/ml 3-Aminotyrosine |
|---|---|---|---|
| 0 | 22.7 | 20.0 | 25.0 |
| 250 | 16.7 | 14.1 | 15.9 |
| 500 | 7.1 | 7.7 | 7.7 |
| 1000 | 1.9 | 2.2 | 2.2 |

B. Zero Hour Incubation: Ratios of Percent Survival

| Dose (rads) | 100 nanomoles/ml 3-Aminotyrosine/ Control[2] | 2 micromoles/ml 3-Aminotyrosine/ Control[2] |
|---|---|---|
| 250 | 0.85 | 0.89 |
| 500 | 0.70 | 0.63 |
| 1000 | 0.56 | 0.51 |

C. Sixteen Hour Incubation: Final Cell Density/Initial Cell Density[3]

| Dose (rads) | Control | 100 nanomoles/ml 3-Aminotyrosine | 2 micromoles/ml 3-Aminotyrosine |
|---|---|---|---|
| 0 | 79.9[4] | 83.3 | 71.4 |
| 250 | 14.2 | 50.5 | 34.6 |
| 500 | 4.2 | 5.3 | 6.1 |
| 1000 | 1.5 | 1.3 | 1.1 |

D. Sixteen Hour Incubation: Ratios of Percent Survival

| Dose (rads) | Number of Cells Seeded | 100 nanomoles/ml 3-Aminotyrosine/ Control[2] | 2 micromoles/ml 3-Aminotyrosine/ Control[2] |
|---|---|---|---|
| 250 | 1000 | 0.81 | 0.84 |
| 250 | 2000 | 0.85 | 0.94 |
| 500 | 1000 | 0.63 | 1.20 |
| 500 | 2000 | 0.98 | 1.59 |
| 1000 | $2.5 \times 10^5$ | 4.91 | 1.95 |

TABLE 4-continued

Ratios of Final to Initial Cell Density in Growth Curve Experiment and Ratios of Percent Survival In Soft Agar Assay - L5178Y Murine Lymphosarcoma Cells

| 1000 | $5.0 \times 10^5$ | 1.27 | 3.22 |

[1] Cells exposed to radiation immediately after treatment with 0.05 ml distilled water (control) or 0.05 ml solution of 3-aminotyrosine.
[2] Ratio of number of colonies surviving in samples treated with 0.05 ml solution 3-aminotyrosine to number of colonies surviving in samples treated with 0.05 ml distilled water (control).
[3] Cells exposed to radiation 16 hours after treatment with 0.05 ml distilled water (control) or 0.05 ml solution of 3-aminotyrosine.
[4] Average of two growth curve experiments.

each flask) with 10 ml of fresh medium; the flasks were then reincubated at 37° C. for 1 hour. After this time, under yellow light, 0.05 ml aliquots of distilled water or solutions of 3-aminotyrosine were injected to give 1:200 dilutions. The flasks were then incubated at 37° C. either for 10 min prior to irradiation, or for 24 hours prior to irradiation. Flasks were irradiated at 0, 250, 500, or 1000 rads at room temperature as previously described. Efforts were made to keep light exposure to a minimum. For those flasks irradiated for 8 min (10 Gy), the temperature in the flasks would decrease during that interval to 30° C.

Immediately after the irradiations were complete, the attached cells were washed two times with Saline A salt solution, the trypsinized using standard procedures with 1.5 ml of trypsin-EDTA (GIBCO 610-5300). The cells were declumped after inactivation of the trypsin with fresh medium, and the cell density determined by Coulter counter. Cell dilutions of appropriate densities were made with fresh medium in sterile plastic conical centrifuge tubes, and 5 ml aliquots were seeded at two different dilutions for each treatment flask into fresh T-25 flasks (4 replicate flasks at each cell dilution). The flasks were all incubated for 7 days, at which time the old medium was aspirated and the cells were fixed in situ with 100% methanol. The colonies were then stained with 0.3% methylene blue, and rinsed with distilled water. After air drying, colonies greater than 1 mm in diameter were scored as viable colonies. The cloning efficiency in each flask was determined as described for the L5178Y cells above. The results are presented in FIG. 6 and Table 5.

Figure 7:
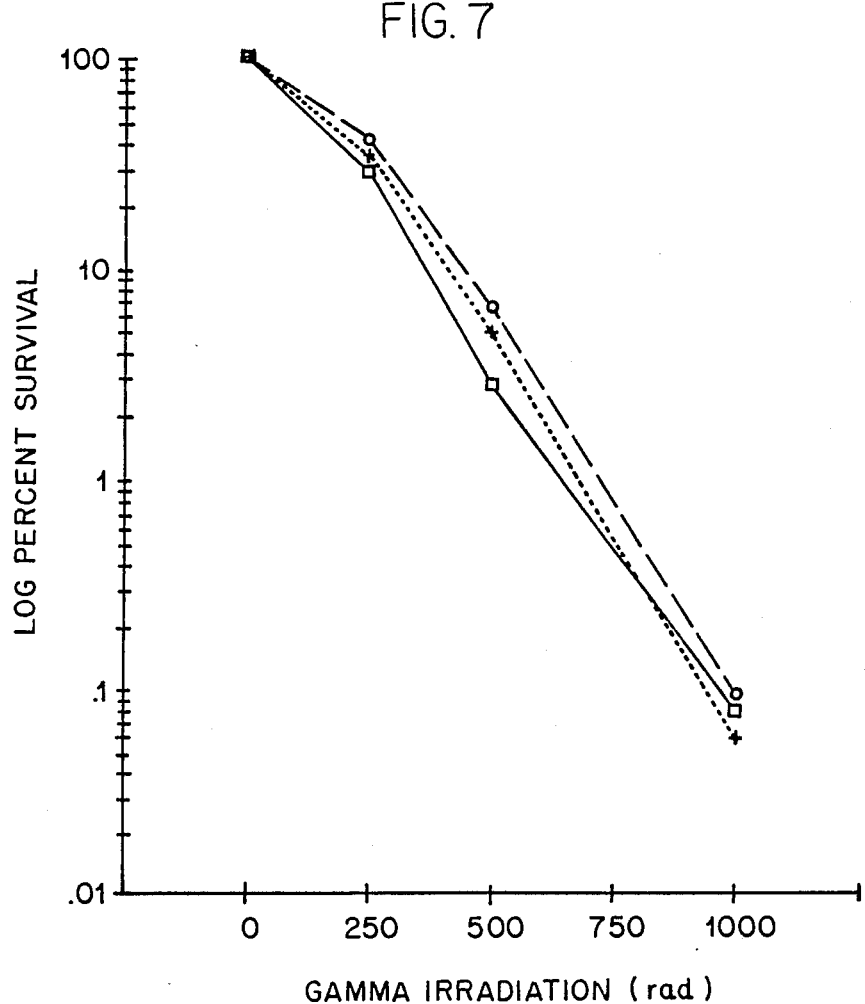
FIG. 7 is a graph showing the log percent survival of human KBE epidermoid carcinoma cells grown on media containing no phenol red as a function of gamma irradiation dosage after 24 hours of incubation in 100 nanomoles/ml (—■—) and 2 micromoles/ml (—0—) solutions of 3-aminotyrosine at 0, 250, 500 and 1000 rads (...+...=control).

In one experiment, treatment with 3-aminotyrosine was performed using custom formulated Earle's BME medium without phenol red (GIBCO 85-0078). Prior to addition of 3-aminotyrosine, cells were washed free of the standard growth medium using Saline A without phenol red. The specially formulated medium with the distilled water control and the 100 nanomoles/ml or 2 micromoles/ml solutions of 3-aminotyrosine were then added as described above for 10 min or 24 hours incubations prior to irradiation. The flasks in this case were gassed with 5% $CO_2$/95% air, since HEPES buffer was also not included in the treatment medium. Results are presented in FIG. 7 and Table 5.

TABLE 5

Ratios of Percent Survival in Soft Agar Assay - Epidermoid Carcinoma Cells

A. Zero Hour Incubation[1]

| Dose (rads) | 100 nanomoles/ml 3-Aminotyrosine/ Control[2] | 2 micromoles/ml 3-Aminotyrosine/ Control[2] |
|---|---|---|
| 250 | 0.94 | 1.70 |
| 500 | 0.81 | 1.25 |
| 1000 | 0.99 | 2.26 |

TABLE 5-continued

Ratios of Percent Survival in Soft Agar Assay - Epidermoid Carcinoma Cells

A. Zero Hour Incubation[1]

| Dose (rads) | 100 nanomoles/ml 3-Aminotyrosine/ Control[2] | 2 micromoles/ml 3-Aminotyrosine/ Control[2] |
|---|---|---|
| B. Twenty-Four Hour Incubation (Phenol Red Present)[3] | | |
| 250 | 1.53 | 1.28 |
| 500 | 1.36 | 2.91 |
| 1000 | 1.63 | 4.65 |
| C. Twenty-Four Hour Incubation (No Phenol Red)[3] | | |
| 250 | 0.79 | 1.08 |
| 500 | 0.48 | 1.49 |
| 1000 | 2.32 | 2.61 |

[1]Cells exposed to radiation immediately after treatment with 0.05 ml distilled water (control) or 0.05 ml of 3-aminotyrosine solution.
[2]Ratio of number of colonies surviving in samples treated with 0.05 ml 3-aminotyrosine solution to number of colonies surviving in samples treated with 0.05 ml distilled water (control).
[3]Cells exposed to radiation 16 hours after treatment with 0.05 ml distilled water (control) or 0.05 ml of 3-aminotyrosine solution.

TEST RESULTS ATTAINED BY USE OF THE PREFERRED EMBODIMENT AND THE PROCESS

Regression of Novikoff Hepatomas in Rats

Young female Sprague-Dawley rats were intraperitoneally inoculated each with 0.5 ml of a Novikoff hepatoma cell suspension. Five days later, the tumors had developed and, in most cases, ascites fluid was present in the peritoneal cavity. At this point, each rat was injected intraperitoneally with 5 mg ICCOPS suspended in a 1% glucose solution. The following day the rats were again given 5 mg ICCOPS, and this was repeated on the third day. Control experiments were done by injecting ICCOPS from which either the glucose oxidase or the peroxidase was omitted or by injecting only the glucose solution. Five days after the last treatment, four of the seven animals treated with the complete ICCOPS system were sacrificed together with all the control animals that were still alive. All control animals had developed massive abdominal tumors amounting to as much as 25 grams of tumor tissue. The animals treated with the complete ICCOPS system, on the other hand, showed the presence of some yellow fibrous connective tissue, but no signs of active tumor growth. The three animals that were saved remained alive for eight months with no apparent ill effects (see Table 6).

Thus far, a total of 24 Novikoff hepatoma bearing rats have been treated with the complete ICCOPS system. A complete regression of the tumor tissue occurred in each one of the animals, and , in all cases, no apparent ill effects were present following the treatment.

TABLE 6

Remission of Novikoff Hepatoma Tumors in Inoculated Rats

| Treatment | Remission |
|---|---|
| HRP-GOD-BSA (3 days) | 15/17 |
| HRP-BSA (3 days) | 0/2 |
| GOD-BSA (3 days) | 0/3 |
| LPO-GOD-BSA (5 days) | 4/4 |
| None | 0/5 |

Effect on ICCOPS on Hepatoma Tumors

A young female rat was inoculated intraperitoneally with 0.5 ml of Novikoff hepatoma cell suspension and the tumor was allowed to develop for five days. At this point, the abdominal cavity was opened under anesthesia. Typical tumor development was observed accompanied by ascites. The abdominal cavity was subsequently close and 5 mg ICCOPS was injected i.p. The rat was subsequently given two more doses of 5 mg ICCOPS on two consecutive days following the first administration, and the abdominal cavity was opened again on the tenth day after the last treatment. At this point, the tumor was converted to a hard, nodular, yellow fibrous mass. The rat subsequently bred two months later and produced a normal litter. This experiment illustrated that the peroxidase promoted tumor regression occurs by means of tumor cell lysis. Most of the ICCOPS particles were found in the omental tissue. Apparently, there is little or no direct contact between the ICCOPS particles and the tumor cells, suggesting that the cytotoxic activity of the ICCOPS particles is transferred to the tumor cells via one or more soluble intermediates.

Histopathological Analysis

A hematoxylin and eosin preparation of the activity growing Novikoff hepatoma was studied. The tumor cells appeared to be of epithelial origin and little connective tissue stroma or encapsulation was evident. The cells were poorly differentiated. The tumor consisted of a continuum of cells forming occasional small cystic appearing structures. The tissue showed an occasional limited differentiation towards pseudorosettes of the cells around the vasculature, and in some areas attempted differentiation towards a papillary pattern. Mitotic figures were common. Vascularity was limited and there were numerous areas of necrosis present in the tissue. The tumor was therefore designated an undifferentiated carcinoma with some characteristics of a papillary cystic adenocarcinoma.

The same preparation of the yellow remains of the tumor taken ten days after the final treatment with ICCOPS was studied. The tissue consisted of islands of necrotic cells encapsulated by an active fibroblastic response. There was a marked collapse of the neoplastic tissue and necrosis appeared to be total. The tissue thus demonstrated tissue necrosis with secondary fibroplasia.

The mesenteric lymph nodes of the same animal showed disruption by an infiltration of neoplastic cells into the nodes. The neoplastic cells had started the formation of discrete islands of tissue, which is indicative of active neoplastic metastasis. Thus, this animal had already suffered metastasis when the primary tumor was being destroyed. If this observation is representative of the other animals, one can only conclude that any metastasized tumor was subsequently destroyed, since all remaining rats fully recovered.

Effect of Peroxidase Inhibitors

In order to obtain additional evidence that the observed tumor regression was indeed promoted by the ICCOPS system, we did an experiment in which some animals were injected with a potent peroxidase inhibitor. The DOPA analog 3-aminotyrosine is a potent inhibitor of horseradish peroxidase with $K_1$ of 5 $\mu$M. Similarly, 3-aminotyrosine has been shown to inhibit T cell (spleen) peroxidase activity.

In this experiment, we administered ICCOPS to eight hepatoma-bearing rats. Four of the animals were also injected with 100 $\mu$g of 3-aminotyrosine.

The results indicated that the 3-aminotyrosine inhibited the action of ICCOPS and all four rats that received 3-aminotyrosine eventually died of the tumor, whereas the four rats receiving ICCOPS only showed complete remission. This confirms that the regression of the hepatomas is indeed promoted by the ICCOPS.

Effect of ICCOPS on Normal Tissue

Two of the male rats with regressed Novikoff hepatomas were sacrificed on the tenth day following the treatment with ICCOPS in order to evaluate the effects of the treatment on fast proliferating normal cells. For this purpose, we examined the testes of the animals by electron microscopy and found that the Sertoli cells and spermatogenesis appeared completely normal.

We also injected 100 mg of ICCOPS into three normal healthy animals on three consecutive days. On the fourth day, one of the animals was sacrificed. Microscopic examination showed that the ICCOPS particles were again embedded in the omental tissue. The other two rats were kept alive for another six months. During this time, we did not observe anything that distinguished them from any other normal healthy animal.

Effect of ICCOPS on Other Tumors

In order to determine whether or not the cytotoxic action of ICCOPS in vivo is specific for rat adenocarcinomas, we tested the effect of ICCOPS on several types of tumors.

A malignant mouse melanoma (B16-F1) was grown in mice, and after an appreciable amount of tumor cells were present in the animals, treatment with ICCOPS was initiated. The results showed that tumor necrosis occurs as a result of the ICCOPS treatment. However, treatment for four to five consecutive days was necessary to obtain complete remission.

We also treated several spontaneous rat breast tumors. In these cases, 5 mg ICCOPS was injected in the proximity of the tumor for three to four consecutive days. A biopsy, taken ten days after the last day of treatment, showed that complete remission of the tumor had occurred. Pathological examination revealed that both a spontaneous breast carcinoma and a breast sarcoma could successfully be treated with ICCOPS.

Furthermore, we treated a dog with advanced Hodgkin's disease (a malignant lymphoma). ICCOPS was injected directly into one of the diseased lymph nodes for three days. At that point, the dog died. However, severe necrosis of the lymphoma was observed in the treated lymph nodes, indicating that this lymphoma is also sensitive to the action of ICCOPS.

Finally, in a similar manner, we achieved a complete remission of a benign tumor (a fibroadenoma) in a rat.

These data indicate that at least several types of tumors are affected by the cytotoxic activity of ICCOPS, and animals bearing such tumors can successfully be treated in this manner. Our data indicate, however, that not all tumors respond equally well to ICCOPS treatment; a different treatment schedule is required for each type of tumor in order to achieve complete remission.

Enhancement of Tumor Growth by Aminotyrosine

In order to evaluate whether or not endogenous peroxidases play a role in the natural resistance to neoplastic growth, we injected some rats with a potent inhibitor of the cytotoxic activity of peroxidases and subsequently challanged the animals with a suspension of hepatoma cells.

Four adult male rats were injected i.p. with 1 mg of 3-aminotyrosine in 1 ml of water. Four control rats were injected with 1 ml of water. The following day all rats were injected with 1 ml of a dilute Novikoff hepatoma cell suspension; the number of cells being normally insufficient to produce tumor growth. On the same day, an additional 1 mg aminotyrosine was administered to the rats that received the inhibitor the previous day and this was repeated for three more days. The four control rats similarly received water injections.

On the ninth day following the inoculation with tumor, all rats were sacrificed and examined for the presence of tumor. No tumor was present in any of the control animals. On the other hand, each of the animals that were treated with aminotyrosine had developed tumor growth. One rat had a large central omental tumor, whereas the other three rats contained a number of small tumors scattered through the mesenteric omentum and over the surface of the small intestines.

This dramatic difference indicates that 3-aminotyrosine inhibits the natural mechanism by which the animal protects itself against neoplasia. As such, its action is similar to that of various immune suppressant compounds.

Effects of ICCOPS on the Immune System

Table 7 illustrates the change in response to Concanavalin A stimulation of spleen cells obtained from tumor-bearing rats and from rats with regressed tumors as compared to normal healthy animals. The data show that spleen cells from tumor-bearing animals are highly active in incorporating thymidine and are insensitive to further stimulation by Concanavalin A. In fact, even at low concentrations, the mitogen acts as an inhibitor. Spleen cells obtained from animals with regressed tumors, on the other hand, can be stimulated by the mitogen, even though they are more active than the cells from healthy rats.

When spleen cells from animals with actively regressing tumors were tested, we observed a pattern similar to that of animals with completely regressed tumors (Table 7). These results suggest that the changes in the immune response occur soon after the administration of ICCOPS. Similar results were obtained with spleen cells of rats previously immunized with KLH (Table 8).

TABLE 7

Responses of Rat Spleen Cells to Concanavalin A In Tumor-Bearing Rats and Rats with Regressing Tumors (5 days after Treatment)

| Con A | Normal Rats CPM[a] | SI[b] | Tumor-Regressing Rats CPM | SI | Tumor-Bearing Rats CPM | SI |
|---|---|---|---|---|---|---|
| 0 | 1165 ± 34 | 1.0 | 6341 ± 1266 | 1.0 | 23343 ± 284 | 1.0 |
| 1 ug | 1409 ± 34 | 1.2 | 10062 ± 946 | 1.6 | 25357 ± 817 | 1.0 |
| 10 ug | 2627 ± 127 | 2.2 | 12854 ± 1203 | 2.0 | 23084 ± 482 | 0.98 |
| 50 ug | 3130 ± 860 | 2.7 | 3028 ± 214 | 0.48 | 17970 ± 3855 | 0.77 |

TABLE 7-continued

Responses of Rat Spleen Cells to Concanavalin A
In Tumor-Bearing Rats and Rats with
Regressing Tumors (5 days after Treatment)

| Con A | Normal Rats CPM[a] | SI[b] | Tumor-Regressing Rats CPM | SI | Tumor-Bearing Rats CPM | SI |
|---|---|---|---|---|---|---|
| 100 ug | 1346 ± 36 | 1.2 | 1833 ± 832 | 0.29 | 2150 ± 813 | 0 |

[a]CPM of tritiated-thymidine taken up by $2 \times 10^5$ cells ± the standard deviation for 3 samples.
[b]SI = Stimulation index: mitogen induced response divided by the control response without mitogen.

TABLE 8

The Specific Immune Response (Secondary) to KLH
By Spleen Cells From Normal, Tumor-Regressing,
and Tumor-Bearing Immunized Rats

| KLH | Normal Rats CPM | SI* | Tumor-Regressing Rats CPM* | SI | Tumor-Bearing Rats CPM | SI |
|---|---|---|---|---|---|---|
| 0 | 386 ± 62 | 1.0 | 3865 ± 61 | 1.0 | 18295 ± 122 | 1.0 |
| 1 ug | 557 ± 57 | 1.4 | 3967 ± 688 | 1.0 | 10288 ± 387 | 0.6 |
| 10 ug | 1973 ± 407 | 5.1 | 6705 ± 600 | 1.7 | 10712 ± 115 | 0.6 |
| 100 ug | 598 ± 118 | 1.5 | 6501 ± 359 | 1.7 | 13442 ± 226 | 0.7 |

*The stimulating index (SI) and the mean CPM ± 5.0, were determined as in TABLE 7.

Again, the cells of animals with actively regressing tumors behaved more like cells from normal animals in their response to stimulation with KLH than like cells from tumor-bearing animals. These data indicate that changes in the immune system occur concomitantly with the tumor regression as a result of the action of the peroxidase system. Whether these changes occur as a result of the regressing tumor or are directly caused by the presence of the peroxidase system cannot be ascertained at the present time.

Prevention of Oxidative Injury

Tables 1 and 9–12 contain data obtained with blood cells from pooled blood of 2 pigs. Tables 2 and 3 contain data derived from cells from a different pig. The concentration of blood cells used in securing data for Tables 1–3, 9, 10 and 12 was adjusted to $9 \times 10^8$ per ml. Table 11 data was derived from RBCs at a concentration of $1.4 \times 10^9$ per ml. Data in Table 11 was corrected for RBC concentration to compare Table 9 (4° C. control) to Table 11 data.

Table 9 shows that pig RBCs (6 days post-collection) displayed only insignificant increases in hemolysis at 43° C. in the presence of 10 mM lactate or pyruvate. There was no change in RBCs in PBS (pH 7.4) without additional reagents. Furthermore, there was no distinction between microwave and hot-air heating effects.

Table 10 indicates that labeling pig RBCs (11–14 days post-collection) with Con A-Lu-BSA sensitized the cells to thermal hemolysis at 43° C. for 10 min. Comparison of the 4° C. controls of Tables 9 and 10 suggest that there was no significant change in thermal fragility during the 6 to 14 day post-collection time frame and that Con A-Lu-BSA coated cells were no more fragile than uncoated cells at 4° C. Furthermore, there appeared to be no significant benefit in storing pig RBCs in inosine (10 mM) in respect to thermal fragility.

In collecting data for Table 11, cells that would show significant thermal fragility were intentionally selected and exposed to conditions that would express this sensitivity. The cells were used at 20 days post-collection. At 48° C. for 30 min in PBS, those cells showed a 61% increase in hemoglobin release above the 4° C. control of Table 9. Mimosine at a final concentration of 340 μM had no effect on the hemolysis.

TABLE 9

| | 43° C. (10 min) | | |
|---|---|---|---|
| Reagents added | Microwave exposed | Hot air | 4° C. |
| None | 0.387 ± 0.042 (5)** | 0.356 ± 0.059 (3) | 0.371 ± 0.060 (4) |
| Pyruvate (10 mM)+ | 0.374 ± 0.055 (4) | 0.427 ± 0.015 (4) | 0.363 (1) |
| Lactate (10 mM) | 0.424 ± 0.014 (4) | 0.440 ± 0.078 (4) | 0.362 (1) |

*6 days post collection; 410 nm optical absorbance of 1:2 diluted supernatant.
**Mean ± 1 standard deviation for number of replicates in parentheses; there were no significant differences between any 2 means by Student's t-test ($p >> 0.05$).
+Final concentration.

TABLE 10

| | 43° C. (10 min) | | |
|---|---|---|---|
| Reagents added | Microwave exposed | Hot air | 4° C. |
| None | 0.617 ± 0.03 (4) | 0.632 ± 0.047 (4) | 0.426 ± 0.027 (3)** |
| Pyruvate (10 mM) | 0.646 ± 0.07 (4) | 0.646 ± 0.02 (4) | |
| Lactate (10 mM) | 0.643 ± 0.02 (4) | 0.667 ± 0.04 (4) | |
| Inosine (10 mM) | 0.578 ± 0.045 (4) | 0.597 ± 0.080 (4) | |

*11–14 days post collection; thermal hemolysis measured by 410 nm optical absorbance of 1:2 dilution of supernatants of RBCs.
**Significantly different ($p < 0.05$) from each of the other means by Student's t-test.

TABLE 11

| | 410 nm absorbance** | | Percent difference from controls (corrected) | |
|---|---|---|---|---|
| Reagents added | Actual | Corrected | 48° C. | 4° C. |
| None (4° C. control) | 0.371 ± 0.039 | 0.371 | −37.8+ | 0 |
| None (48° C. control) | 0.795 ± 0.029 | 0.596 | 0 | 60.6+ |

TABLE 11-continued

| Reagents added | 410 nm absorbance** | | Percent difference from controls (corrected) | |
|---|---|---|---|---|
| | Actual | Corrected | 48° C. | 4° C. |
| L—mimosine (340 μM) | 0.965 ± 0.026 | 0.724 | 21.5+ | 95.1+ |
| 3-amino-L—tyrosine (74 μM) | 0.491 ± 0.032 | 0.368 | −38.3+ | −0.8 |

*20 days post collection.
**Performed in triplicate and corrected for difference in RBC dilution from 4° C. control.
+Corrected means significantly different from control (p < 0.05) by Student's t-test.

However, 3-amino-L-tyrosine had a profound effect. At a final concentration of 74 μM, 3-amino-L-tyrosine suppressed the thermal hemolysis to the level of the 4° C. control.

Table 12 shows chemiluminescence (CL) of Con A-Lu-BSA labeled pig RBCs ($6 \times 10^7$ cells/sample) in the presence of exogenous hydrogen peroxide (63 mM) and a variety of metabolites and antimetabolites. All assays were run at room temperature. The post-collection age of those cells was 11–18 days and the cells were used the day of labeling. Unlabeled pig RBCs demonstrated a significant amount of natural chemiluminescence in the presence of hydrogen peroxide and base (44% of that of labeled RBCs). Pyruvate (1.43 mM), an autoxidizable substrate, doubled the CL of labeled cells. Lactate at 1.43 mM produced insignificant increases in the CL. However, inosine did produce a small but significant increase in CL (p>0.05). A small but significant decrease in the residual CL (9% decrease, p>0.05) was produced when samples were heated to 48° C. in a waterbath for 30 min.

Robust effects on CL were found with the antimetabolites mimosine and 3-amino-L-tyrosine. At 630 μM, mimosine inhibited the CL by 72%. This level of CL was 36% below natural RBC CL. Prewashing of the labeled cells for 30 min at room temperature in 5 mM mimosine had no significant effect on the CL. Therefore, little if any mimosine entered or adhered to the luminescent sites on the cells. Amino-L-tyrosine at 1.44 mM inhibited the CL of labeled RBCs by 97%. The inhibition was 94% of the natural CL. At 160 μM, 3-amino-L-tyrosine

TABLE 12

| Reagents added | CL (30 sec) | Percent control |
|---|---|---|
| None (control, labeled) | 30,319 ± 1,201 (6) | 100 |
| None (no cells) | 62 ± 7 (3) | 0.2+ |
| Pig RBCs (natural CL) | 13,351 ± 2,119 (4) | 44+ |
| Pyruvate (no cells, 1.43 mM) | 420 (1) | 1.4+ |
| Pyruvate (1.43 mM) | 60,732 ± 3,258 (4) | 200+ |
| Lactate (1.43 mM) | 30,930 ± 3,399 (5) | 102 |
| Inosine (1.43 mM) | 34,972 ± 2,732 (4) | 115+ |
| L—mimosine (630 μM) | 8,555 ± 1,044 (3) | 28+ |
| pretreatment (5 mM)** | 28,517 ± 2,591 (3) | 94 |
| 3-Amino-L—tyrosine | | |
| (1.44 mM) | 844 ± 165 (4) | 3+ |
| (160 μM) | 5,430 ± 1,266 (3) | 18+ |
| pretreatment (11.5 mM) | 22,457 ± 2,128 (3) | 74+ |
| None (48° C., 30 min) | 27,637 ± 1,162 (3) | 91+ |

*100 μl 1:30 dilution of RBCs, 11–18 days post collection, activated by addition of 500 μl 0.3% $H_2O_2$ in pH 7.4 PBS and 100 μl 0.1 N NaOH.
**Cells were incubated in this solution for 30 min and washed before activation.
+Means significantly different (p < 0.05) from control by Dunnett's test.

inhibited the CL of labeled RBCs by 82%. Some absorption of 3-amino-L-tyrosine was noted with pretreatment of labeled cells with 11.5 mM 3-amino-L-tyrosine (30 min at room temperature) based on the 26% inhibition of CL.

The cumulative effect of hydrogen peroxide exposure on the nonspecific binding of Lu-BSA is shown in Table 1. Exposure of $1.4 \times 10^9$ RBCs/ml to 44 mM $H_2O_2$ for 15 min at 37° C. (hot air) resulted in a 721% increase in bound Lu-BSA as measured by base activated CL when compared to cells maintained in PBS, pH 7.4, for 15 min at 37° C. The post-collection age of these RBCs was 19 days. As noted in Table 8, the natural CL of unlabeled cells treated with base was 5 counts/30 s.

Data from blood cells used within the first 24 hours after being drawn is shown in Table 2. An overnight incubation at 4° C. was used in the labeling of the cells in Table 2 rather than the 30 min at 37° C. technique. 3-amino-L-tyrosine demonstrates its antioxidative properties by inhibiting the effects of hydrogen peroxide at 37° C. Binding induced by hydrogen peroxide (11.7 mM) was inhibited 51% by 1.49 mM 3-amino-L-tyrosine. This level of inhibition brought the binding within 14% above the 37° C. control.

Heating the cells used in Table 2 without additional reagents to 45° C. for 30 min (water bath) increased the binding of Lu-BSA 58% above the 4° C. control, but only an insignificant 3% above the 37° C. control. The presence of pyruvate (1.33 mM) during exposure to 45° C. increased the binding by 101% over the 45° C. exposure alone.

The addition of 3-amino-L-tyrosine (1.49 mM) did not significantly inhibit thermal hemolysis at 45° C. The mean spontaneous hemolysis of the 27 samples (Table 2) was 0.251±0.01 as measured by the optical density of the sample supernatants (1:2 dilution) at 410 nm. Only when the RBCs were treated with 3-amino-L-tyrosine and $H_2O_2$ at 37° C. there was a significant increase in the hemolysis above the 4° C. control (0.261±0.007, compared to 0.243±0.004, p>0.005 by Student's t test, unpaired, two-tailed).

Table 3 reports data using the same source of cells as was used for Table 2. However, the cells were used 72 hours post-collection. Also, the cells were labeled by incubating the Lu-BSA with the RBCs for 30 min at 37° C. In an attempt to prevent an anticipated increase, some of the RBCs were stored at 4° C. in 1.49 mM 3-amino-L-tyrosine for 72 hours prior to use. There was an apparent protection of the RBCs since they bound 10% less Lu-BSA than those stored in PBS. The 3-amino-L-tyrosine was not replaced with fresh reagent during the 30 min incubation at 37° C. Treatment of the RBCs with pyruvate (1.33 mM) for 30 min at 37° C. increased the Lu-BSA binding 2.7 times. Using cells that had been preincubated in 3-amino-L-tyrosine protected them from the effects of pyruvate. The mean baseline spontaneous hemolysis for the 37° C. control was 0.340 for two samples. For samples treated with pyruvate and pyruvate and 3-amino-L-tyrosine, the spontaneous hemolysis readings at 37° C. were 0.362±0.016 (n=3) and 0.326±0.03 (n=3), respectively. Preincubation with 3-amino-L-tyrosine alone led to a value significantly (p>0.005) higher in each case than those of cells subjected to other treatments. The hemolytic value for 3-amino-L-tyrosine was 0.452±0.02 (n=4).

The results of cloning efficiency and percent survival studies of L5178Y cells are plotted on FIG. 3. No difference in the reproductive integrity of the cells, at any of the three dose levels tested, is evident. This is substantiated by the ratios of percent (%) survival in Table 11A, which, even at the high chemical concentration, never exceed 1.0, indicating no protection.

When the percent (%) survival values for cells preincubated for 16 hours in 3-aminotyrosine are examined, there is some evidence from FIG. 4, and Table 4, that 3-aminotyrosine is protective of cell survival. This evidence is also indicated by the ratios of % survival for the 500 and 1000 rad doses, which are both above 1.0.

Table 5 and FIG. 5 summarize the data for chemical addition immediately prior to the exposure. As indicated on FIG. 5, the 0 dose (control) cloning efficiencies were very similar; in this experiment, a laboratory control was also performed without addition of 3-aminotyrosine.

Cloning efficiencies were determined at each radiation dose with 4 replicate dishes seeded at two different cell densities. The 0 rad cloning efficiency for each concentration of 3-aminotyrosine is the average for all eight dishes at the two different densities needed. At the higher dose, the average percent survival plotted is that obtained for the dishes seeded at the lower cell innoculum. Table 5 and FIG. 6 summarize the data for chemical addition 24 hours prior to exposure into medium containing phenol red.

In this experiment, the 0 dose (100% survival value) for cloning efficiency was the average of 4 replicate plates seeded with the lower cell number. The values were calculated and plotted as described above. Again in this experiment, the high concentration of 3-aminotyrosine shows higher survival than the low chemical concentration, indicating a radioprotective effect. This effect is clearly evident from the radios of percent (%) survival values (Table 5) where a protective effect is indicated also for the low chemical concentration.

The low-dose radioprotection after pre-incubation in 3-aminotyrosine for 24 hours in comparison to no radioprotection at 10 minute preincubations (0 hours) indicates a cumulative effect of 3-amino-L-tyrosine. The accumulation of 3-amino-L-tyrosine protection suggest that low doses could be administered to an animal or human over several days prior to irradiation or exposure to other stimuli to achieve the same level of protection as a single high concentration dose.

This thermal protectant effect of 3-aminotyrosine may be used to advantage for such purposes as the long-term storage of RBCs. For such purposes, a carbohydrate energy source which maintains the ATP levels of the cells must also be added. For instance, for storage of blood, one part of 3.8% sodium citrate solution containing 2 mg D-glucose and 100 nanomoles of 3-amino-L-tyrosine per ml may be added to 9 parts of blood. The blood is then refrigerated at 4° C. until used for interveneous administration. Inosine, adenosine or ribose may be used instead of D-glucose in a ratio of about 10 micromoles per milliliter of blood.

CONCLUSION

The data presented in this application show that IC-COPS, an immobilized system with glucose oxidase and horseradish peroxidase as its functional components, rapidly and selectively destroys a very malignant and advanced adenocarcinoma in rats. In addition, other malignant tumors, including a melanoma, a sarcoma and a lymphoma, are subject to selective destruction by ICCOPS. Previous in vitro studies by others using soluble glucose oxidase and horseradish peroxidase showed no specificity for tumor cells as compared with normal cells. A similar lack of specificity was observed with the myeloperoxidase and lactoperoxidase systems. In our in vivo study, on the other hand, a very high degree of selectivity was obtained as illustrated by two facts. Firstly, no obvious damage was found to normal tissues, including to rapidly proliferating testicular cells; and secondly, the histopathological tissue slices show that fibroblasts located adjacent to necrosing tumor cells are essentially normal.

We also found that the peroxidase system activates a secondary antitumor mechanism. This secondary system appears to be the cell-mediated portion of the immune system. The spontaneous blastogenic activity of spleen cells of rats with actively growing tumor indicates a maximally stimulated immune system that fails to produce an effective response. Introduction of IC-COPS, however, rapidly modifies the immune system by reducing the ineffective response and restoring the mitogenic and specific immune response. These results indicate that ICCOPS acts as an immunostimulant in animals whose normal response is insufficient. The increased sensitivity of animals toward a challenge with tumor cells as a result of 3-aminotyrosine administration, thus acting as an immunosuppressant, also supports this conclusion. Hence, ICCOPS, as well as peroxidase inhibitors, could also be useful as therapeutic agents in diseases affecting the immune system, in regulating the immune system following organ transplants, and other tissue implantations, as well as in any therapy that requires either a suppression or activation of the endogenous immune response.

Mimosine is a known peroxidase and tyrosinase inhibitor. Hashiguchi, H. and H. Takahashi, "Inhibition of two copper-containing enzymes, tyrosinase and dopamine $\beta$-hydroxylase, by L-mimosine," 13 Molec. Pharm. 362–367 (1977), Christie, G.S., et al., "Antithyroid properties of 3-hydroxy-4(1-H)-pyridone: Antiperoxidase activity and effect on thyroid function," 195 Endocrinology 342–347 (1979). The data presented herein indicates that 3-aminotyrosine is oxidizable and acts as either a peroxidase inhibitor or alternate substrate. The antimetabolites mimosine and 3-amino-L-tyrosine could interact with methemoglobin, functioning as a peroxidase and catalyzing the thermally induced autoxidation of red blood cells. As the data in Table 11 demonstrates, mimosine at 340 $\mu$M failed to protect against thermal hemolysis at 48° C. for 30 min. However, 3-amino-L-tyrosine at a much lower concentration (74 $\mu$M) proved to be a powerful inhibitor. When hydrogen peroxide was added to RBCs ($9 \times 10^7$) labeled with Con A-Lu-BSA, a high level of CL was produced (see Table 12). This CL was inhibited by mimosine and 3-amino-L-tyrosine. As might be anticipated from the hemolysis data, 3-amino-L-tyrosine was a more effective inhibitor of CL than mimosine, perhaps through a different mechanism since mimosine acts as an uncompetitive inhibitor of 3-aminotyrosine oxidation by peroxidase. Pyruvate acted as a co-oxidant, inosine slightly but significantly enhanced CL, and lactate was relatively inert in the CL reaction. At the appropriate concentrations, both mimosine and 3-amino-L-tyrosine reduced the CL of the RBCs below the background level of peroxide-induced CL of natural membrane components. The effectiveness of 3-amino-L-tyrosine in protecting these natural membrane components from oxidation is probably related to its thermoprotective properties.

Experiments involving the nonspecific binding of Lu-BSA to RBCs (Tables 1, 2 and 3) indicate that hydrogen peroxide and pyruvate increase the labeling. These oxidants probably work through the formation of dialdehydes by membrane oxidation. The aldehydes in turn bind the Lu-BSA through aldimine (Schiff base) formation.

The binding of 3-amino-L-tyrosine to the cell membrane via its alpha amino group, and the subsequent inhibition of CL by inhibiting the binding of Lu-BSA, is unlikely. As indicated in Table 12, preincubation with 8 times the 3-amino-L-tyrosine used in the Lu-BSA binding experiments produced only a 26% inhibition of CL, indicating that little of the 3-amino-L-tyrosine was retained at the membrane surface. The subsequent washing removes loosely bound 3-amino-L-tyrosine and the addition of the Lu-BSA at pH 6.9 favors BSA binding by the Schiff base reaction. Also, the 3-amino-L-tyrosine readily, autoxidizes like dihydroxyphenylalanine (DOPA), probably forming an internally cyclized colored product; therefore, the oxidation is likely to eliminate the alpha amino group. The yellowing of 3-amino-L-tyrosine solutions with age is evidence of the oxidation.

The data in Tables 2 and 3 supports the concept that 3-amino-L-tyrosine thermoprotects through an anticatalytic antioxidative mechanism, and the cumulative effects of RBC oxidation can be measured by the Lu-BSA binding assay. Samples treated with 3-amino-L-tyrosine and $H_2O_2$ showed a significant increase in spontaneous hemolysis. Also, cells preincubated in 3-amino-L-tyrosine alone for 72 hours showed a significantly higher spontaneous hemolysis than those subjected to the other treatments. These results, when taken with the CL data, indicate that the spontaneous hemolysis or thermal fragility taken as a point reading is not a good indicator of physiological aging or previous oxidative injury. The 3-amino-L-tyrosine data indicate that the baseline fragility of stored cells is not just a function of oxidative mechanisms, although such mechanisms do contribute to cell membrane stability.

There are, of course, many variations to the specific steps, techniques, dosage, materials, and the like, used in our work described herein. Additionally, all equivalents to the preferred embodiment expressly described herein are intended to be encompassed with the following claims.

What is claimed is:

1. A process for protecting mammalian cells in vitro from an oxidative source, said process comprising:
   (a) determining the oxidative source, said oxidative source selected from the group comprising heat and ionizing radiation, whereby the cell damage protected from includes lethality, functional loss, genetic damage and membrane permeability; and
   (b) applying a predetermined amount of 3-aminotyrosine to said mammalian cells at a concentration ranging between about 74 nanomoles per milliliter of cells to about 2 millimoles per mililiter of cells sufficient to protect said mammalian cells from said oxidative source.

2. A process as defined in claim 1 wherein said mammalian cells are selected from the grouping consisting of red blood cells, primary tissue isolates and established cell lines.

3. A process as defined in claim 1 wherein 3-aminotyrosine is 3-amino-L-tyrosine.

4. A process for preserving a sample of mammalian blood cells in vitro, said process comprising:
   (a) applying 3-aminotyrosine to said sample at a concentration ranging between about 74 nanomoles per milliliter of blood cells to about 1.44 micromoles of 3-aminotyrosine per milliliter of blood cells is added to said sample; and adding a carbohydrate energy source to maintain adequate levels of adenosine triphoshate in the same.

5. A process as defined in claim 4 wherein said carbohydrate energy source is selected from the group consisting of ribose, inosine, glucose, and adenosine.

6. A process as defined in claim 4 wherein said sample of cells is maintained at a temperature of about 4 degrees centigrade.

* * * * *